US010416111B2

(12) United States Patent
Okamoto et al.

(10) Patent No.: US 10,416,111 B2
(45) Date of Patent: Sep. 17, 2019

(54) GAS SENSOR

(71) Applicant: NGK INSULATORS, LTD., Nagoya-shi, Aichi (JP)

(72) Inventors: Taku Okamoto, Nagoya (JP); Noriko Hirata, Nagoya (JP); Yuki Nakayama, Nagoya (JP); Kosuke Monna, Nukata-gun (JP)

(73) Assignee: NGK INSULATORS, LTD., Nagoya (JP)

( * ) Notice: Subject to any disclaimer, the term of this patent is extended or adjusted under 35 U.S.C. 154(b) by 149 days.

(21) Appl. No.: 15/611,053

(22) Filed: Jun. 1, 2017

(65) Prior Publication Data
US 2018/0011051 A1 Jan. 11, 2018

(30) Foreign Application Priority Data
Jul. 8, 2016 (JP) .................................. 2016-135969

(51) Int. Cl.
*G01N 27/407* (2006.01)
(52) U.S. Cl.
CPC ..... *G01N 27/4077* (2013.01); *G01N 27/4074* (2013.01); *G01N 27/4076* (2013.01)
(58) Field of Classification Search
CPC ............... G01N 27/4074; G01N 27/406–4078
See application file for complete search history.

(56) References Cited

U.S. PATENT DOCUMENTS

| 6,254,749 | B1 * | 7/2001 | Yokota | G01N 27/4074 204/424 |
| 8,133,370 | B2 | 3/2012 | Roessler et al. | |
| 2003/0205078 | A1 * | 11/2003 | Hasei | G01N 27/4074 73/23.31 |
| 2016/0033447 | A1 | 2/2016 | Nakasone et al. | |

FOREIGN PATENT DOCUMENTS

| JP | 4402282 B2 | 1/2010 |
| JP | 4914447 B2 | 4/2012 |
| JP | 5883976 B2 | 3/2016 |

* cited by examiner

*Primary Examiner* — J. Christopher Ball
(74) *Attorney, Agent, or Firm* — Global IP Counselors, LLP

(57) ABSTRACT

A mixed-potential type gas sensor capable of preferably determining the concentration of THC including a kind of gas having a large C number is provided. A sensor element composed of an oxygen-ion conductive solid electrolyte is provided with, on its surface, a sensing electrode formed of a cermet of Pt, Au, and an oxygen-ion conductive solid electrolyte, and includes a reference electrode and a porous surface protective layer that covers at least said sensing electrode. An Au abundance ratio on a surface of noble metal particles forming the sensing electrode is 0.3 or more. The surface protective layer has a porosity of 28% to 40%, a thickness of 10 to 50 μm, and an area ratio of a coarse pore having a pore size of 1 μm or larger of 50% or more; or has a porosity of 28% to 40% and a thickness of 10 to 35 μm.

3 Claims, 11 Drawing Sheets

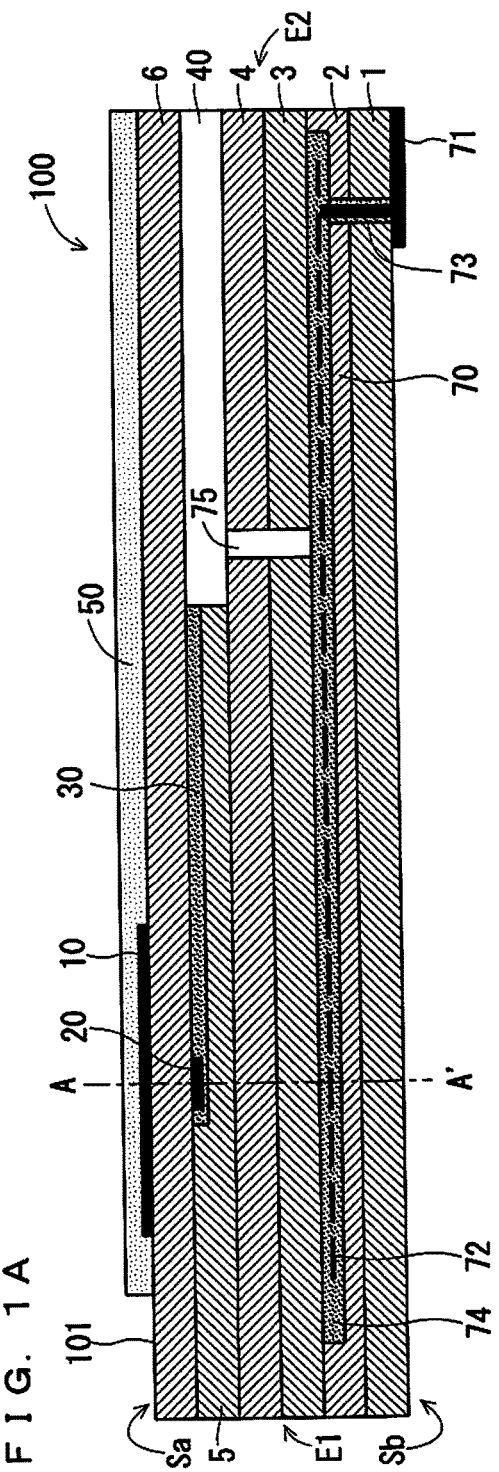
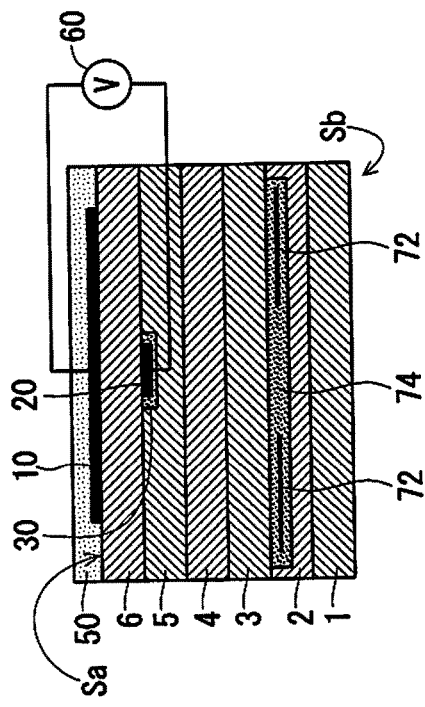
FIG. 1A
FIG. 1B

F I G . 2
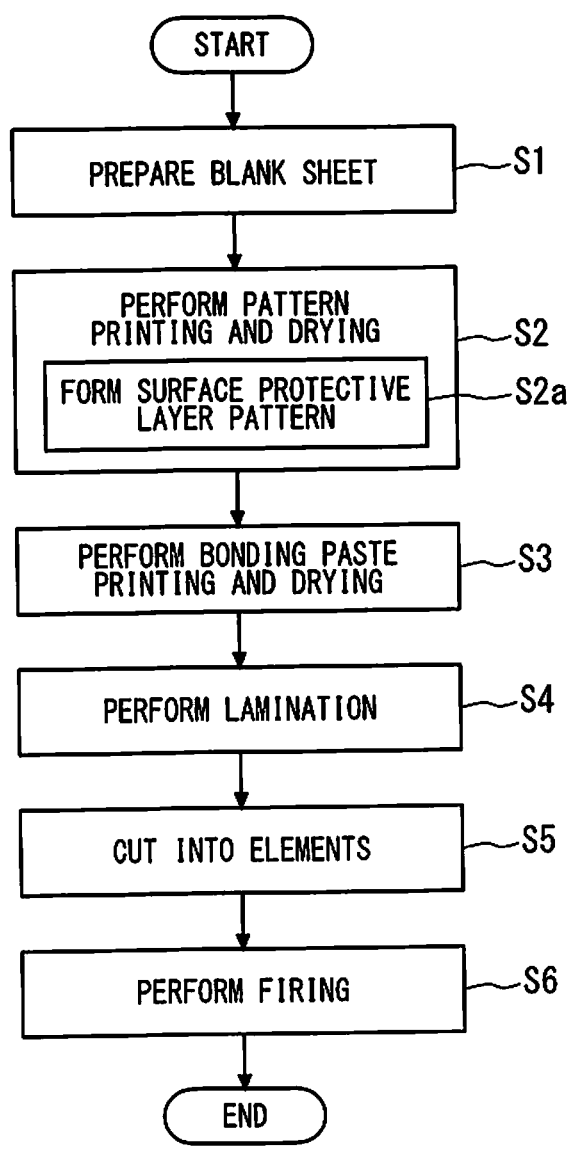

F I G . 3
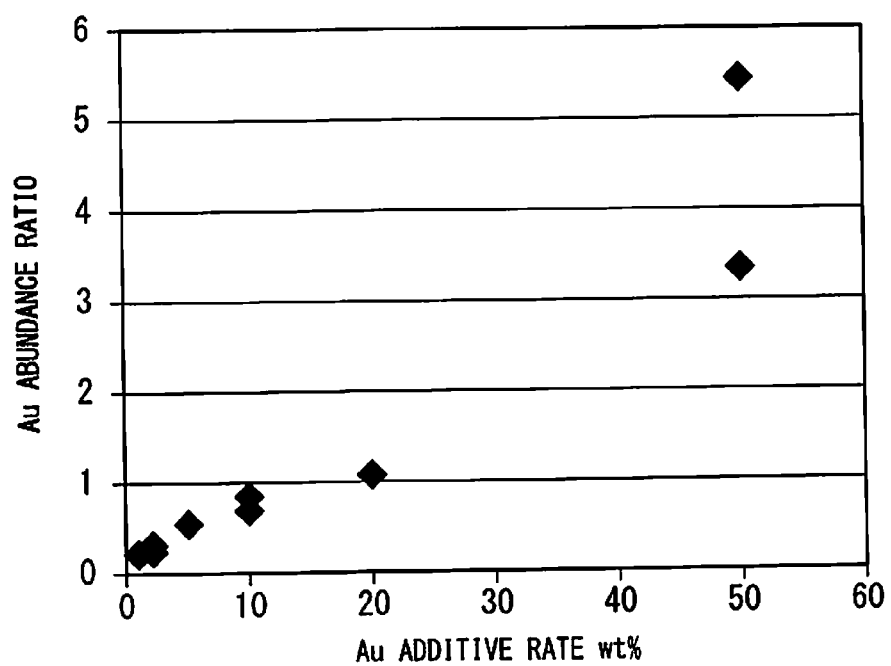

F I G . 9
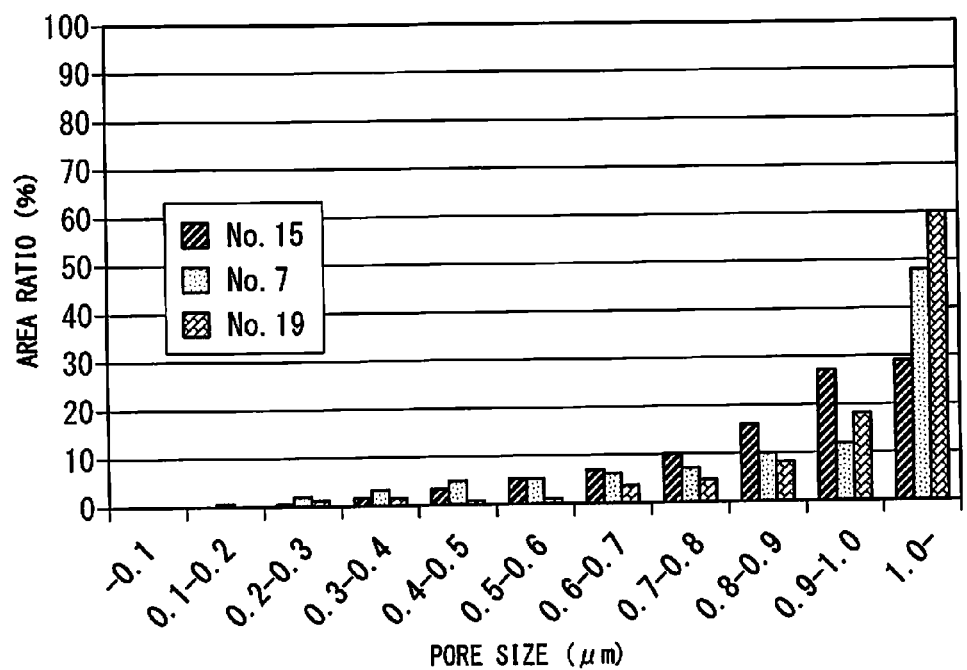

FIG. 10A
FIG. 10B
FIG. 10C
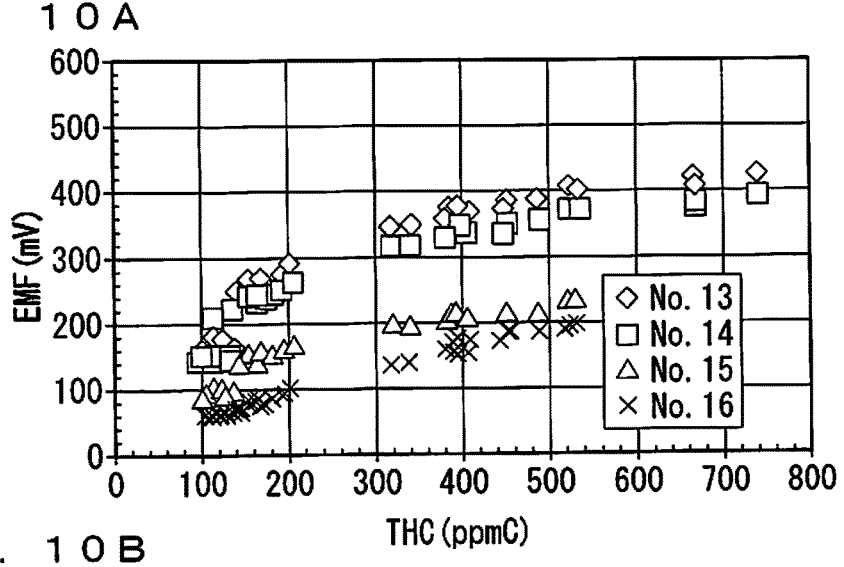
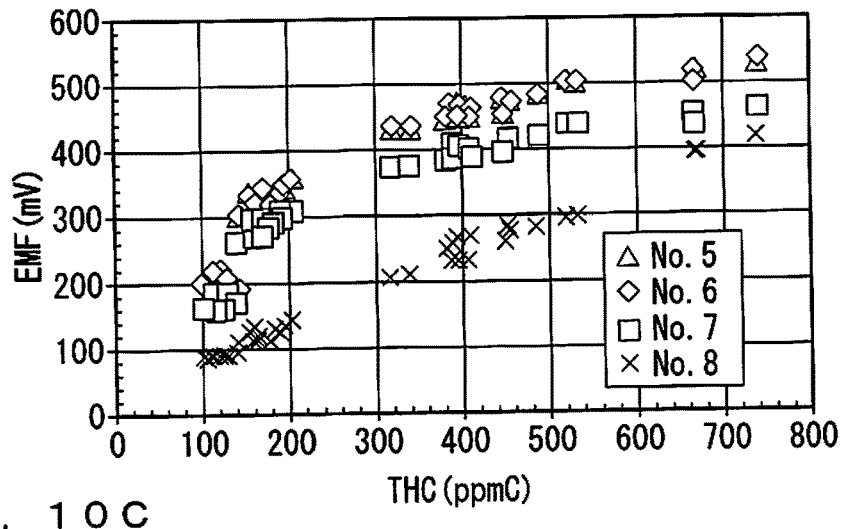
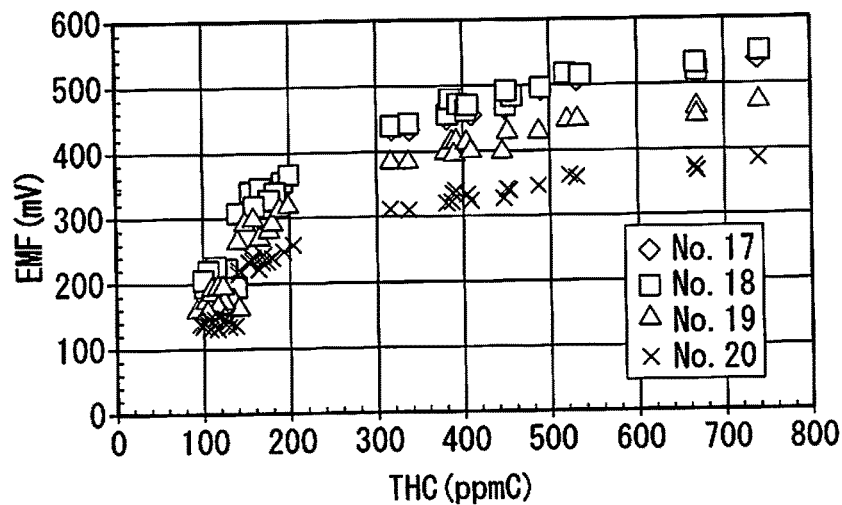

F I G. 1 1 A
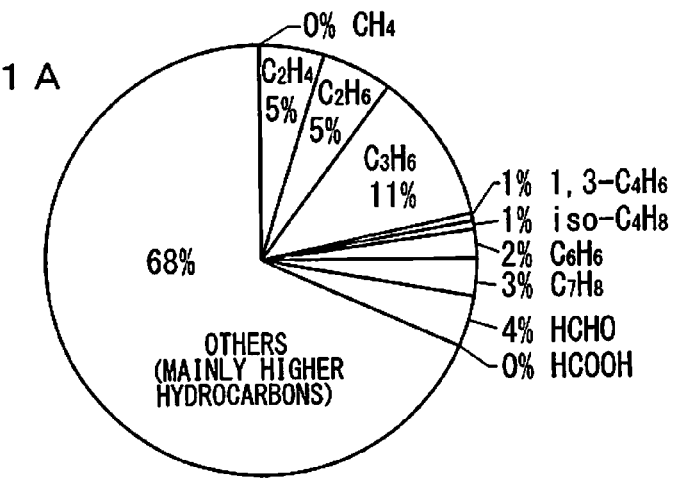
F I G. 1 1 B
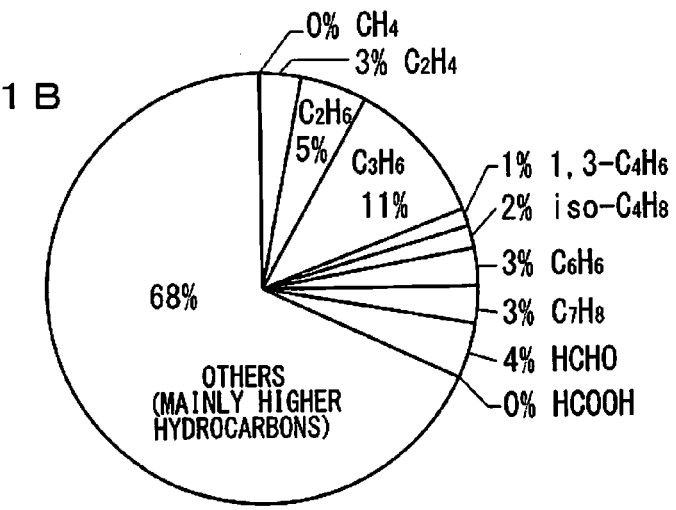
F I G. 1 1 C
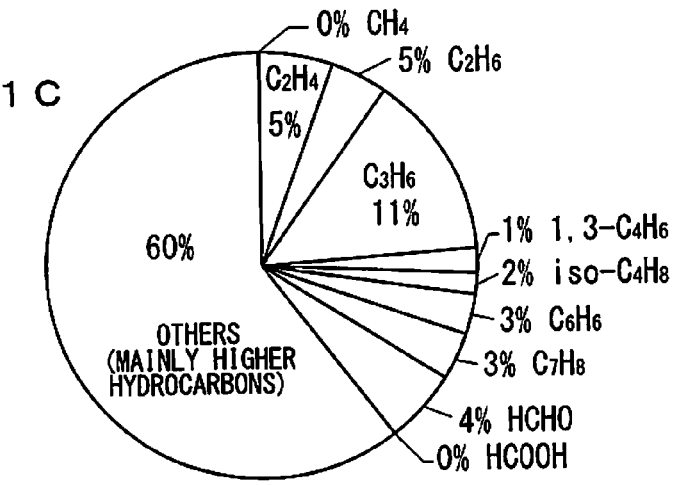

GAS SENSOR

BACKGROUND OF THE INVENTION

Field of the Invention

The present invention relates to a gas sensor used to measure a hydrocarbon gas concentration, and particularly relates to a protective layer provided to a sensor element thereof.

Description of the Background Art

Measurement of the concentration of a hydrocarbon gas included in an exhaust gas has been increasingly required because of recent reinforcement of exhaust gas regulation. Known gas sensors (hydrocarbon gas sensors or HC sensors) used to measure the concentration of hydrocarbon gas each include a sensor element mainly formed of a solid electrolyte (for example, Japanese Patent No. 4914447, Japanese Patent No. 4402282, and Japanese Patent No. 5883976).

Japanese Patent No. 4914447 discloses a gas sensor configured to determine the concentration of a gas based on a potential difference that occurs between two electrodes provided on opposite surfaces or the same surface of a support formed of a solid electrolyte.

Japanese Patent No. 4402282 discloses a mixed-potential type hydrocarbon gas sensor including a two-layer sensing electrode on the outer surface of a bottomed cylindrical solid electrolyte body and including a reference electrode on the inner surface thereof.

Japanese Patent No. 5883976 discloses a hydrocarbon gas sensor including a sensing electrode on the surface of a sensor element that is a laminated body of solid electrolyte layers, and including a reference electrode disposed in a reference gas atmosphere inside the element.

Some conventionally known hydrocarbon gas sensors each include a protective layer on the surface of the sensor element. The protective layer functions, for example, to protect the sensing electrode provided on the surface of the element from any poisoning substance (for example, phosphorus) and to increase the durability of the sensor element. However, the protective layer needs to be provided not only to preferably achieve these functions but also not to encumber expected performance of the sensor element. In particular, when provided to cover the sensing electrode provided on the surface of the element, the protective layer needs to be provided so as not to prevent arrival of a measurement gas at the sensing electrode. If the arrival of a measurement gas at the sensing electrode is prevented, the responsiveness (capability of achieving real-time measurement) and the measurement accuracy of the hydrocarbon gas sensor cannot be achieved, which is not preferable.

Hydrocarbons collectively refer to many kinds of compounds each made of carbon (C) and hydrogen (H). An engine exhaust gas contains, various kinds of hydrocarbons such as a hydrocarbon having a small carbon number (C number) and thus a small molecular size (small molecular weight), and a hydrocarbon having a large C number and thus a large molecular size (large molecular weight). It is important for the exhaust gas regulation to regulate all hydrocarbons (total hydrocarbon (THC)). Thus, a hydrocarbon gas sensor is required to be capable of measuring the THC.

FIGS. 11A, 11B, and 11C show pie charts of the abundance ratios of various kinds of (unburned) hydrocarbons in the THC included in an exhaust gas ejected from a typical diesel engine (displacement 2.0 L, in-line four cylinder). FIGS. 11A, 11B, and 11C show the abundance ratios when the exhaust temperature is 200° C., 300° C., and 400° C. To obtain the pie charts shown in FIGS. 11A, 11B, and 11C, the abundance ratios of CO, $CH_4$, $C_2H_4$, $C_2H_6$, $C_3H_6$, $C_4H_6$, $C_4H_8$, $C_6H_6$, $C_7H_8$, HCHO, and HCOOH were calculated based on a result of concentration measurement using an FTIR (MEXA-6000FT manufactured by HORIBA). Then, the total abundance ratio of other (mainly higher hydrocarbon) THC was calculated based on a value obtained by subtracting the sum of the concentrations of these materials from a total THC concentration measured by an FID (MEXA-7500D manufactured by HORIBA). A higher hydrocarbon is defined to have a C number of 8 or more. In FIGS. 11A, 11B, and 11C, 0% indicates that the abundance ratio of the corresponding material is less than 1%.

FIGS. 11A, 11B, and 11C indicate that materials having C numbers of 6 or more account for 75% approximately or more of the THC included in an exhaust gas, and have a ratio approximately three times larger than that of materials having C numbers of 4 or less. This indicates that accurate THC measurement requires reliable sensing of any hydrocarbon having a large C number. No CO was detected.

Study on a relation between the formation manner of the protective layer in a sensor element and the measurement performance of a hydrocarbon gas sensor, which was carried out by the inventor of the present application invention, found that the THC measurement performance of the hydrocarbon gas sensor is affected by a relation between the formation manner of the protective layer and the C number or molecular size of a hydrocarbon gas.

However, Japanese Patent No. 4914447 and Japanese Patent No. 5883976 both give description that the sensor element includes the protective layer, but no description on the relation between the formation manner of the protective layer and the C number or molecular size of a hydrocarbon gas.

Japanese Patent No. 4402282 discloses such a technology that the protective layer is formed on the sensing electrode and the poisoning substance is intentionally adsorbed at least with the protective layer in advance, so that a stable output is achieved even when a poisoning substance is adsorbed. Japanese Patent No. 4402282 discloses, as exemplary detected gasses, various kinds of hydrocarbon gasses having different C numbers. However, the protective layer provided to the sensor element disclosed in Japanese Patent No. 4402282 is dense and thick with a relative density of 94% or more and a thickness of 100 μm to 300 μm, and thus cannot sufficiently sense any hydrocarbon having a large C number. Japanese Patent No. 4402282 only discloses, in a preferred embodiment, an evaluation example in which propene having a C number of 3 is used as a model gas, but does not disclose nor hint capability of preferably sensing a hydrocarbon having a large C number.

SUMMARY OF THE INVENTION

The present invention relates to a gas sensor used to measure a hydrocarbon gas concentration, and is directed particularly to a protective layer provided to a sensor element included in the gas sensor.

According to the present invention, a mixed-potential type gas sensor for sensing a hydrocarbon gas in a measurement gas includes a sensor element composed of an oxygen-ion conductive solid electrolyte. The sensor element includes: a sensing electrode formed of a cermet of a noble metal and an oxygen-ion conductive solid electrolyte, the sensing electrode being provided on a surface of the sensor element; a reference electrode formed of a cermet of Pt and an oxygen-ion conductive solid electrolyte; and a surface protective layer being a porous layer that covers at least the sensing electrode. The noble metal is Pt and Au. An Au abundance ratio being an area ratio of a portion covered with the Au to a portion at which the Pt is exposed in a surface of noble metal particles forming the sensing electrode is 0.3 or more. The surface protective layer has a porosity of 28% or more and 40% or less, a thickness of 10 μm or larger and 50 μm or smaller, and an area ratio of a coarse pore of 50% or more, the area ratio of the coarse pore being a ratio of an area of coarse pores each having a pore size of 1 μm or larger to the total area of all pores, or has a porosity of 28% or more and 40% or less and a thickness of 10 μm or larger and 35 μm or smaller. The sensor element is configured and arranged to determine a concentration of the hydrocarbon gas on the basis of a potential difference between the sensing electrode and the reference electrode.

Accordingly, a gas sensor is achieved that is capable of measuring, at an accuracy allowing its practical use, the concentration of total hydrocarbon gas in a measurement gas containing a plurality of kinds of hydrocarbon gasses such as a hydrocarbon gas having a large carbon number, and does not suffer the occurrence of clogging of a poisoning substance at a surface protective layer even when continuously used.

It is preferable that the surface protective layer has a porosity of 28% or more and 40% or less, a thickness of 10 μm or larger and 35 μm or smaller, and the area ratio of the coarse pore of 50% or more.

Accordingly, a gas sensor is achieved that is capable of reliably sensing a hydrocarbon gas having a large carbon number and included in a measurement gas, and is capable of measuring the concentration of total hydrocarbon gas in the measurement gas at an excellent accuracy.

An object of the present invention is to provide a gas sensor capable of preferably sensing the concentration of the THC containing a kind of gas having a large carbon number.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 1A and 1B are schematic sectional views schematically illustrating an example configuration of a gas sensor 100 according to a preferred embodiment of the present invention;

FIG. 2 shows a flow of the processing of manufacturing a sensor element 101;

FIG. 3 shows an Au abundance ratio in a sensing electrode 10 formed of a conductive paste for forming a sensing electrode, which is plotted against an Au additive rate in a starting raw material when the conductive paste is prepared through liquid-state Au mixing;

FIG. 9 shows pore size distributions of the gas sensors 100 of No. 15, No. 7, and No. 19;

FIGS. 10A, 10B, and 10C show the sensitivity characteristics of all gas sensors 100 of types A to C; and FIGS. 11A, 11B, and 11C each show a pie chart of abundance ratios of various kinds of (unburned) hydrocarbons in THC included in an exhaust gas ejected from a typical diesel engine.

DESCRIPTION OF THE PREFERRED EMBODIMENTS

<Example Configuration of Gas Sensor>

Figure 4A:
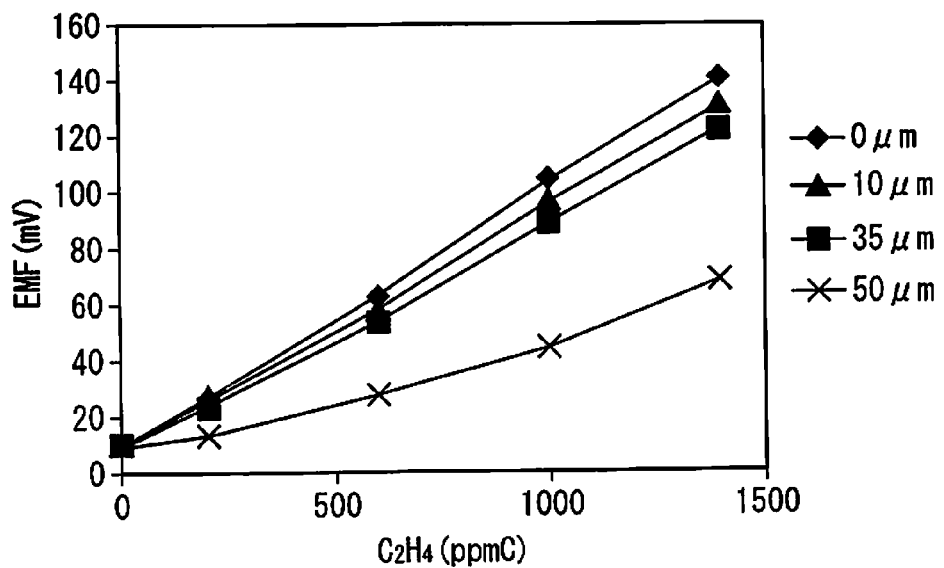
FIGS. 4A and 4B show sensitivity characteristics for $C_2H_4$ and n-C8.

FIGS. 1A and 1B are schematic sectional views schematically illustrating an example configuration of a gas sensor 100 according to a preferred embodiment of the present invention. FIG. 1A is a vertical sectional view of a sensor element 101, which is a main component of the gas sensor 100, taken along the longitudinal direction of the sensor element 101. FIG. 1B is a view including a cross-section of the sensor element 101 perpendicular to the longitudinal direction of the sensor element 101 at a position A-A' of FIG. 1A.

The gas sensor 100 according to this preferred embodiment is a so-called mixed-potential type gas sensor. Generally speaking, the gas sensor 100 determines the concentration of a gas component, which is a measurement target, in a measurement gas using a potential difference that occurs between a sensing electrode 10, which is provided on the surface of the sensor element 101 mainly made of ceramic that is an oxygen-ion conductive solid electrolyte such as zirconia ($ZrO_2$), and a reference electrode 20, which is provided inside the sensor element 101, due to a difference in the concentration of the gas component between the portions near the electrodes based on the principle of mixed potential.

More specifically, the gas sensor 100 preferably determines the concentration of total hydrocarbon (THC), which is all unburned hydrocarbon gasses in a measurement gas, where the measurement gas is an exhaust gas present in an exhaust pipe of an internal combustion engine such as a diesel engine or a gasoline engine. In the present specification, the unburned hydrocarbon gasses includes carbon monoxide (CO) in addition to typical hydrocarbon gasses (categorized into hydrocarbons when expressed in a chemical formula) such as $C_2H_4$, $C_3H_6$, and n-C8 ($C_8H_{18}$).

As described above, since the exhaust gas includes the unburned hydrocarbon gasses at ratios shown in FIGS. 11A, 11B, and 11C, the abundance ratios of these plurality of kinds of unburned hydrocarbon gasses are reflected on the potential difference that occurs between the sensing electrode 10 and the reference electrode 20 in the gas sensor 100.

The sensor element 101 mainly includes a reference gas introduction layer 30, a reference gas introduction space 40, and a surface protective layer 50 in addition to the sensing electrode 10 and the reference electrode 20 described above.

In this preferred embodiment, the sensor element 101 has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101 additionally includes other components mainly between these layers or on an outer peripheral surface of the element. The solid electrolytes constituting these six layers are fully airtight. Such a sensor element 101 is manufactured by, for example, laminating ceramic green sheets corresponding to the individual layers, which have been subjected to a predetermined process and printing of a circuit pattern, and further, by integrating the laminated layers through firing.

The gas sensor 100 does not necessarily need to include the sensor element 101 formed of such a laminated body including the six layers. The sensor element 101 may be formed as a laminated body having more or fewer layers or may not have a laminated structure.

In the following description, for convenience' sake, the surface located as the upper surface of the sixth solid electrolyte layer 6 in FIGS. 1A and 1B is referred to as a front surface Sa of the sensor element 101, and the surface located as the lower surface of the first solid electrolyte layer 1 in FIGS. 1A and 1B is referred to as a rear surface Sb of the sensor element 101. In the determination of the concentration of the THC in a measurement gas with the gas sensor 100, a predetermined range starting from a distal end E1 being one end of the sensor element 101, which includes at least the sensing electrode 10, is disposed in a measurement gas atmosphere; the other portion including a base end E2 opposite to the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position closer to the distal end E1 that is one end in the longitudinal direction of the sensor element 101 on the front surface Sa of the sensor element 101. The gas sensor 100 is placed such that, in its use, the sensor element 101 corresponding to at least the portion in which the sensing electrode 10 is provided is exposed to a measurement gas.

The catalytic activity of the sensing electrode 10 against unburned hydrocarbon gas is disabled by preferably determining the composition of the Pt—Au alloy being its constituent material. That is, the decomposition reaction of the unburned hydrocarbon gas is prevented or reduced in the sensing electrode 10. In the gas sensor 100, accordingly, the potential of the sensing electrode 10 selectively varies with respect to (has correlation with) the THC in accordance with its concentration. In other words, the sensing electrode 10 is provided so as to have high dependence of potential on concentration for the THC while having low dependence of potential on concentration for other components of the measurement gas. This will be described below in detail.

The reference electrode 20 is an electrode having a substantially rectangular shape in plan view, which is provided inside the sensor element 101 and serves as a reference in the determination of the concentration of the measurement gas. The reference electrode 20 is provided as a porous cermet electrode of Pt and zirconia.

The reference gas introduction layer 30 is a layer made of porous alumina, which is provided inside the sensor element 101 to cover the reference electrode 20. The reference gas introduction space 40 is an internal space provided near the base end E2 of the sensor element 101. Air (oxygen), serving as a reference gas in the determination of the concentration of the THC, is externally introduced into the reference gas introduction space 40.

The reference gas introduction space 40 and the reference gas introduction layer 30 are in communication with each other, and accordingly, in the use of the gas sensor 100, the surrounding of the reference electrode 20 is always filled with air (oxygen) through the reference gas introduction space 40 and the reference gas introduction layer 30. During the use of the gas sensor 100, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even when the sensing electrode 10 is exposed to the measurement gas.

In the case illustrated in FIG. 1A, the reference gas introduction space 40 is provided in such a manner that part of the fifth solid electrolyte layer 5 is in communication with the exterior on the base end E2 of the sensor element 101. The reference gas introduction layer 30 is provided so as to extend in the longitudinal direction of the sensor element 101 between the fifth solid electrolyte layer 5 and the sixth solid electrolyte layer 6. The reference electrode 20 is provided under the center of gravity of the sensing electrode 10 with reference to FIGS. 1A and 1B.

The surface protective layer 50 is a porous layer made of alumina, which is provided so as to cover at least the sensing electrode 10 on the front surface Sa of the sensor element 101. The surface protective layer 50 is provided as an electrode protective layer that prevents or reduces the degradation of the sensing electrode 10 due to continuous exposure to a measurement gas during the use of the gas sensor 100. In the case illustrated in FIGS. 1A and 1B, the surface protective layer 50 is provided so as to cover not only the sensing electrode 10 but also substantially the entire front surface Sa of the sensor element 101 except for a predetermined range starting from the distal end E1.

It is preferable that the surface protective layer 50 is formed to have a porosity of 28% or more and 40% or less and a thickness of 10 μm or larger and 35 μm or smaller, and the area ratio of pores (hereinafter referred to as coarse pores) each having a pore size of 1 μm or larger (ratio of an area occupied by coarse pores to the total area of all pores) is preferably 50% or more (hereinafter, these conditions are collectively referred to as a first condition). In such a case, almost all the hydrocarbons included in the THC arrive at the sensing electrode 10 through the surface protective layer 50. Thus, the concentration of the THC is measured at an excellent accuracy by the gas sensor 100. Any poisoning substance is preferably trapped by the surface protective layer 50, causing no clogging due to the poisoning substance at the surface protective layer 50 in continuous use.

In the case that the surface protective layer 50 at least has a porosity of 28% or more and 40% or less, a thickness of 10 μm or larger and 50 μm or smaller, and an area ratio of a coarse pore of 50% or more, or has a porosity of 28% or more and 40% or less and a thickness of 10 μm or larger and 35 μm or smaller (hereinafter, these conditions are collectively referred to as a second condition), the gas sensor 100 can sense, in most cases at a level allowing its practical use, the THC including a hydrocarbon having a large C number, although the reliability is slightly degraded as compared to the case of the surface protective layer 50 satisfying the first condition. Accordingly, the gas sensor 100 can measure the concentration of the THC at an accuracy allowing its practical use. Similarly to the first condition, any poisoning substance is preferably trapped by the surface protective layer 50, causing no clogging due to the poisoning substance at the surface protective layer 50 in continuous use.

A condition with a porosity of less than 28% and a thickness exceeding 50 µm is not preferable because any kind of gas having a large C number is unlikely to reach the sensing electrode 10 through the surface protective layer 50. A condition with a porosity of less than 28% or a condition with a thickness of less than 10 µm is not preferable because clogging of a poisoning substance occurs at the surface protective layer 50 in continuous use. A condition with a porosity exceeding 40% is not preferable because a poisoning substance is likely to directly reach the sensing electrode 10. In the first place, it is not always easy to form the surface protective layer 50 having a porosity exceeding 40%.

In this preferred embodiment, the porosity and pore size distribution are evaluated by analyzing an enlarged cross-sectional SEM image (secondary electron image) (by referencing descriptions in Nobuyasu Mizutani et al., "Ceramic Processing" (GIHODO SHUPPAN Co., Ltd.)).

The thickness of the surface protective layer 50 is defined to be the distance between the outermost surface of the sensing electrode 10 and the outermost surface of the surface protective layer 50 (not the distance between the front surface Sa of the sensor element 101 and the outermost surface of the surface protective layer 50).

As illustrated in FIG. 1B, the gas sensor 100 is equipped with a potentiometer 60 capable of measuring a potential difference between the sensing electrode 10 and the reference electrode 20. Although FIG. 1B schematically illustrates wiring of the sensing electrode 10, the reference electrode 20, and the potentiometer 60, in an actual sensor element 101, connection terminals (not shown) are provided correspondingly to the respective electrodes on the front surface Sa or the rear surface Sb on the base end E2, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. Hereinbelow, a potential difference between the sensing electrode 10 and the reference electrode 20, which is measured by the potentiometer 60, is also referred to as a sensor output.

The sensor element 101 further includes a heater part 70, which performs temperature control of heating the sensor element 101 and maintaining the temperature of the sensor element 101, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101 (in FIGS. 1A and 1B, the lower surface of the first solid electrolyte layer 1). The heater electrode 71 is connected with an external power (not shown), so that the heater part 70 can be powered externally.

The heater 72 is an electric resistor provided inside the sensor element 101. The heater 72 is connected with the heater electrode 71 through the through hole 73 and generates heat by being powered externally via the heater electrode 71 to heat the solid electrolytes forming the sensor element 101 and maintain their temperatures.

In the case illustrated in FIGS. 1A and 1B, the heater 72 is buried while being vertically sandwiched by the second solid electrolyte layer 2 and the third solid electrolyte layer 3 so as to extend from the base end E2 to the position below the sensing electrode 10 near the distal end E1. Accordingly, the entire sensor element 101 can be adjusted to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 and to be in communication with the reference gas introduction space 40, and is formed to mitigate an internal pressure rise associated with a temperature rise in the heater insulating layer 74.

In the determination of the concentration of the THC in a measurement gas using the gas sensor 100 having such a configuration, as described above, air (oxygen) is supplied to the reference gas introduction space 40, with the sensor element 101 in only a predetermined range, which starts from the distal end E1 and includes at least the sensing electrode 10, being disposed in a space containing a measurement gas, and with the sensor element 101 on the base end E2 being apart from the space. The heater 72 heats the sensor element 101 to an appropriate temperature of 400° C. or higher and 800° C. or lower, preferably 500° C. or higher and 700° C. or lower, more preferably 500° C. or higher and 600° C. or lower. The temperature of the sensor element 101 being heated by the heater 72 is also referred to as an element control temperature. In this preferred embodiment, the element control temperature is evaluated from the surface temperature of the sensing electrode 10. The surface temperature of the sensing electrode 10 can be evaluated by infrared thermography.

In this state, a potential difference occurs between the sensing electrode 10 exposed to the measurement gas and the reference electrode 20 exposed to the air. As described above, however, the potential of the reference electrode 20 disposed in the air (having a constant oxygen concentration) atmosphere is maintained at a constant potential, whereas the potential of the sensing electrode 10 selectively has a dependence on concentration for the THC in the measurement gas. Thus, this potential difference (sensor output) substantially becomes a value according to the composition of the measurement gas present around the sensing electrode 10. Therefore, a certain functional relationship (referred to as sensitivity characteristics) holds between the concentration of the THC and the sensor output.

In the actual determination of the concentration of the THC, in advance, a plurality of different mixed gasses, each of which has a known concentration of the THC, are used as the measurement gas, and the sensitivity characteristics are experimentally identified by performing a measurement on the sensor output for each measurement gas. In the actual use of the gas sensor 100, accordingly, an operation processor (not shown) converts the sensor output, which varies from moment to moment in accordance with the concentration of the THC in a measurement gas, into the concentration of the THC based on the sensitivity characteristics. The concentration of the THC in the measurement gas can be determined almost in real time.

In addition, since the surface protective layer 50 satisfies at least the second condition, the gas sensor 100 according to this preferred embodiment can sense, in most cases at a level allowing its practical use, the THC including a hydrocarbon having a large C number. In particular, in the case that the surface protective layer 50 satisfies the first condition, the gas sensor 100 can sense almost all hydrocarbons included in the THC and thus measure the THC at an excellent accuracy.

<Process of Manufacturing Sensor Element>

Next, the process of manufacturing the sensor element 101 will be described using an example case where the sensor element has the layer structure as illustrated in FIGS. 1A and 1B. Generally speaking, the sensor element 101 as illustrated in FIGS. 1A and 1B is manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

FIG. 2 is a flowchart illustrating the process of manufacturing the sensor element 101. In the manufacture of the sensor element 101, first, blank sheets (not shown) that are green sheets having no pattern formed thereon are prepared (step S1). Specifically, six blank sheets corresponding to the first to sixth solid electrolyte layers 1 to 6 are prepared. A plurality of sheet holes used for positioning in printing and lamination are provided in the blank sheets. Such sheet holes are formed in advance through, for example, punching by a punching device. For a green sheet whose corresponding layer forms an internal space, a penetration corresponding to the internal space is also provided in advance through, for example, punching as described above. Not all the blank sheets corresponding to the respective layers of the sensor element 101 need to have the same thickness.

After the preparation of the blank sheets corresponding to the respective layers, pattern printing and dry are performed to form various patterns on the individual blank sheets (step S2). This includes formation of a pattern for forming the surface protective layer 50 in addition to formation of electrode patterns of, for example, the sensing electrode 10 and the reference electrode 20, a pattern for forming the reference gas introduction layer 30, and a pattern for internal wiring (not shown). In the first solid electrolyte layer 1, a cut mark is printed that serves as a reference cut position when the laminated body is cut in a subsequent step.

Each pattern is printed by applying a paste for pattern formation, prepared in accordance with the characteristic required for each formation target, to the blank sheet by a known screen printing technique. For example, the pattern for forming the surface protective layer 50 is formed by printing, to the sixth solid electrolyte layer 6, a protective-layer paste containing alumina powder, a binder, and an organic solvent. Any known drying means is available for dry after printing.

This preferred embodiment is characterized by the way of preparing a conductive paste used to form the sensing electrode 10. This will be described below in detail.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the adhesive-applied green sheets are laminated in a predetermined order, and the laminated green sheets are crimped on the predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body has been obtained as described above, subsequently, a plurality of parts of the laminated body are cut out as individual units (referred to as element bodies) of the sensor element 101 (step S5). The cut-out element bodies are fired under predetermined conditions, thereby producing the sensor element 101 as described above (step S6). In other words, the sensor element 101 is produced by integrally firing the solid electrolyte layers and the electrodes. The firing temperature is preferably 1200° C. or more and 1500° C. or lower (for example, 1370° C.). The integral firing performed in such a manner provides satisfactory adhesion strength to the respective electrodes and the surface protective layer 50 of the sensor element 101.

The resultant sensor element 101 is housed in a predetermined housing and incorporated into a main body (not shown) of the gas sensor 100.

<Details of Electrodes>

As described above, in the gas sensor 100, the sensing electrode 10 is formed such that its catalytic activity against the THC is disabled. This is implemented by including gold (Au) in the sensing electrode 10 as a conductive component (noble metal component), in addition to platinum (Pt) being a main constituent.

Specifically, the sensing electrode 10 is formed so that the abundance ratio (Au abundance ratio) of Au in the sensing electrode 10 is 0.3 or more. In such a case, high sensitivity is achieved as compared to a case where the sensing electrode 10 is formed as a cermet electrode of Pt and zirconia similarly to the reference electrode 20.

In the present specification, the Au abundance ratio is an area ratio of a portion covered with Au to a portion at which Pt is exposed in the surface of the noble metal particles forming the sensing electrode 10. The Au abundance ratio is one when the area of the portion at which Pt is exposed is equal to the area of the portion covered with Au. In the present specification, the Au abundance ratio is calculated using a relative sensitivity coefficient method from peak intensities of peaks detected for Au and Pt obtained by X-ray photoelectron spectroscopy (XPS).

When the Au abundance ratio is 0.3 or more, in the sensing electrode 10, Au is concentrated in the surface of the noble metal particles forming the sensing electrode 10. More specifically, an Au-riched Pt—Au alloy is formed near the surface of Pt-riched Pt—Au alloy particles. In such a state, catalytic activity is preferably disabled in the sensing electrode 10, and the potential of the sensing electrode 10 has enhanced dependence on the concentration of the THC.

The volume ratio between noble metal components and zirconia in the sensing electrode 10 may be 5:5 to 8:2 approximately.

For allowing the gas sensor 100 to preferably exhibit its function, the sensing electrode 10 preferably has a porosity of 10% or more and 30% or less and a thickness of 5 μm or larger. In particular, the sensing electrode 10 more preferably has a porosity of 15% or more and 25% or less and a thickness of 25 μm or larger and 35 μm or smaller.

The plane size of the sensing electrode 10 may be appropriately set, and it suffices that, for example, the sensing electrode 10 has a length of 2 mm to 10 mm approximately in the longitudinal direction of the sensor element, and a length of 1 mm to 5 mm approximately in a direction perpendicular to the longitudinal direction. Since the surface protective layer 50 is formed so as to cover the sensing electrode 10 as described above, the plane size of the surface protective layer 50 is larger than the plane size of the sensing electrode 10.

The reference electrode 20 is preferably formed so as to have a porosity of 10% or more and 30% or less and a thickness of 5 µm or larger and 15 µm or smaller. The plane size of the reference electrode 20 may be smaller than the sensing electrode 10 as illustrated in FIGS. 1A and 1B, or equivalent to the sensing electrode 10.

<Conductive Paste for Forming Sensing Electrode>

Next, a conductive paste used to form the sensing electrode 10 will be described. The conductive paste for forming a sensing electrode is produced by using an Au ion-containing liquid as an Au starting material and mixing the Au ion-containing liquid with powdered Pt, powdered zirconia, and a binder. Any binder, which can disperse any other row material to the printable extent and vanishes through firing, may be appropriately selected. The production of a conductive paste in such a manner is referred to as liquid-state Au mixing.

Here, the Au ion-containing liquid is obtained by dissolving a salt containing an Au ion or an organometallic complex containing an Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the sensing electrodes 10 formed in the sensor element 101 obtained through the above-mentioned manufacturing process contain Au mainly as an elemental substrate or an alloy with Pt.

FIG. 3 shows an Au abundance ratio in the sensing electrode 10 formed of a conductive paste for forming a sensing electrode, which is plotted against an Au weight ratio (hereinafter, referred to as an Au additive rate) to the weight of all the noble metal elements (a total weight of Pt and Au) of starting raw materials in a range where the Au additive rate is 50 wt % or less, where the conductive paste is prepared through liquid-state Au mixing.

FIG. 3 indicates that the sensing electrode 10 having an Au abundance ratio of 0.3 or more can be manufactured when the Au additive rate is 2 wt % or more, and the Au abundance ratio tends to be larger when the Au additive rate is larger. In other words, with the use of a conductive paste having an Au additive rate of 2 wt % or more, the sensing electrode 10 having an Au abundance ratio of 0.3 or more can be preferably formed. However, the Au additive rate is preferably 50 wt % or less. This is because it is difficult to manufacture the sensing electrode 10 having favorable conductivity whose Au additive rate exceeds 50 wt %.

<Another Way of Preparing Conductive Paste>

In the preparation of a conductive paste for forming a sensing electrode, the paste may be prepared by using coated powder, which is obtained by coating powdered Pt with Au, as a starting raw material, instead of preparing the paste through liquid-state Au mixing as described above. In such a case, a conductive paste for a sensing electrode is prepared by mixing the coated powder, zirconia powder, and a binder. Here, the coated powder may be obtained by covering the particle surface of powdered Pt with an Au film or applying Au particles to Pt powder particles.

Also in this case, the sensing electrode 10 having an Au abundance ratio of 0.3 or more can be preferably formed.

EXAMPLES

Experimental Example

Experiments were performed to verify a difference in the sensitivity characteristic of the gas sensor 100 between kinds of gas. Specifically, the sensitivity characteristic was evaluated for $C_2H_4$ and n-C8 ($C_8H_{18}$), which are each a kind of THC in an exhaust gas.

Conditions of measurement of the sensor output (EMF) when each sensitivity characteristic was acquired are listed below. The Au abundance ratio was 0.50 for any gas sensor 100.

Element control temperature: 500° C.;
Gas atmosphere ($C_2H_4$): $O_2$=10%, $H_2O$=5%, $C_2H_4$=0 ppmC, 200 ppmC, 600 ppmC, and 1400 ppmC, balance: $N_2$;
Gas atmosphere ($C_8H_{18}$): $O_2$=10%, $H_2O$=5%, $C_8H_{18}$=0 ppmC, 160 ppmC, 320 ppmC, 480 ppmC, 640 ppmC, 800 ppmC, 960 ppmC, or 1200 ppmC, balance: $N_2$;
Gas flow rate: 5 L/min;
Pressure: 1 atm;
Surface protective layer: porosity=28%, thickness=0 µm (no protective layer), 10 µm, 35 µm, or 50 µm.

Figure 4B:
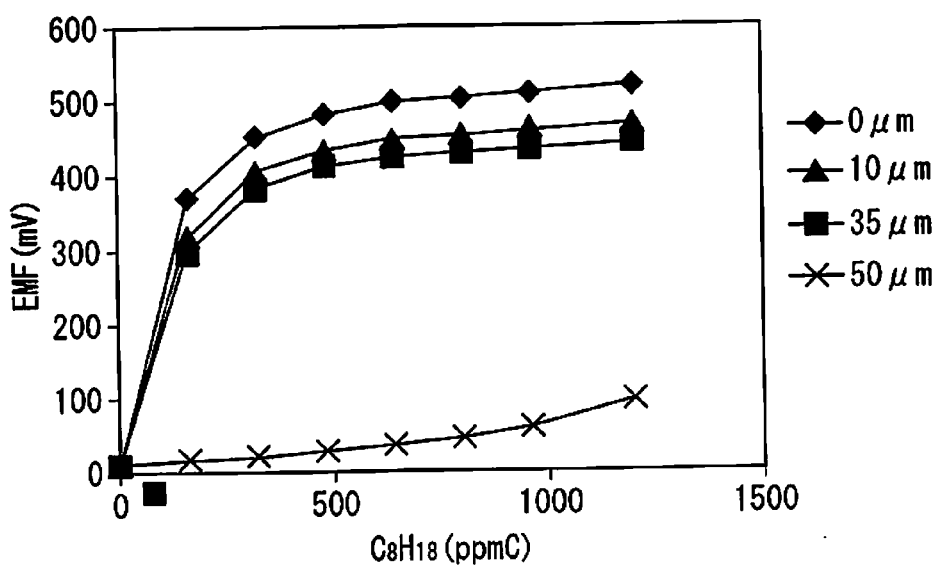

FIGS. 4A and 4B show the sensitivity characteristics thus obtained. FIG. 4A shows a result for $C_2H_4$, and FIG. 4B shows a result for $C_8H_{18}$. Comparison between the results finds that the sensor output tends to be larger in the latter result except when the thickness of the surface protective layer 50 is 50 µm. This indicates that, when the gas sensor 100 performs measurement on the THC originally including the kinds of gas in the abundance ratios as illustrated in FIGS. 11A, 11B, and 11C, the sensor output would become smaller than its original value if a kind of gas such as $C_8H_{18}$ having a large C number does not reach the sensing electrode 10 through the surface protective layer 50.

In both of FIGS. 4A and 4B, the sensor output is small when the surface protective layer 50 has a large thickness of 50 µm. This indicates that forming the surface protective layer 50 to be excessively thick against poisoning is not preferable from the viewpoint of the sensitivity of the gas sensor 100.

This experimental example shows that accurate THC concentration determination requires formation of the surface protective layer 50 such that each kind of gas, particularly a kind of gas having a large C number, arrives at the sensing electrode 10 in the original abundance ratio.

Example 1

In this example, 12 kinds of the gas sensor 100 (No. 1 to No. 12) in each of which the surface protective layer 50 has different combinations of a porosity and a thickness, were prepared and subjected to evaluation of their sensitivity characteristics to THC and a phosphorus poisoning test. Specifically, the porosity was varied in three levels: 40%, 28%, and 12%, and the thickness was varied in four levels:

5 μm, 10 μm, 35 μm, and 50 μm. The Au abundance ratio was 0.50 for any gas sensor 100. The firing temperature at the manufacture of the sensor element 101 was 1370° C.

The porosity of the surface protective layer 50 was controlled by using different particle sizes of an alumina raw material as a raw material of the surface protective layer 50. Specifically, the porosity of the surface protective layer 50 was varied in three levels described above by using three kinds of alumina raw material having different relative surface areas each correlated with the particle size. The porosity of the surface protective layer 50 and the relative surface area of the alumina raw material have the following correspondence relations.

Porosity of 40%←Relative surface area of 2.5 m$^2$/g;
Porosity of 28%←Relative surface area of 8.4 m$^2$/g;
Porosity of 12%←Relative surface area of 60 m$^2$/g.

The evaluation of the porosity was performed with analysis of an image obtained by capturing of an SEM image of a cross-section of the surface protective layer 50 at an acceleration voltage of 5 kV, and then enlarging the capture image 7500 times.

Table 1 lists a combination of the porosity and thickness of the surface protective layer 50 of each gas sensor 100.

TABLE 1

| SENSOR NO. | PROTECTIVE LAYER POROSITY | PROTECTIVE LAYER THICKNESS (μm) | SENSITIVITY CHARACTERISTIC EVALUATION | POISONING TEST RESULT |
|---|---|---|---|---|
| 1 | 40% | 5 | ○ | x |
| 2 | 40% | 10 | ○ | ○ |
| 3 | 40% | 35 | ○ | ○ |
| 4 | 40% | 50 | ○ | ○ |
| 5 | 28% | 5 | ○ | x |
| 6 | 28% | 10 | ○ | ○ |
| 7 | 28% | 35 | ○ | ○ |
| 8 | 28% | 50 | Δ | ○ |
| 9 | 12% | 5 | Δ | x |
| 10 | 12% | 10 | Δ | x |
| 11 | 12% | 35 | x | x |
| 12 | 12% | 50 | x | x |

Figure 5:
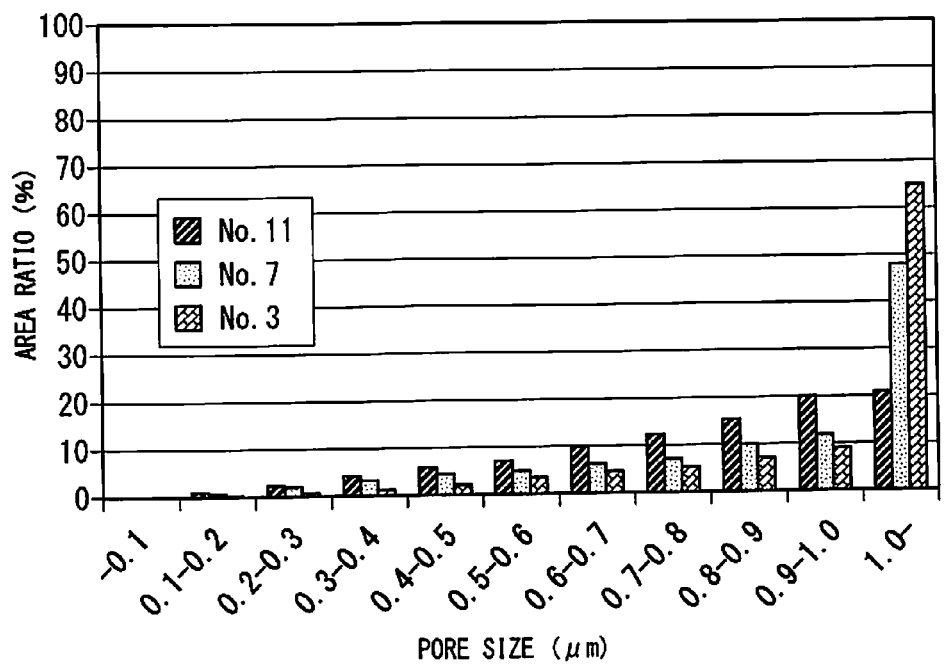
FIG. 5 shows pore size distributions of the gas sensors 100 of No. 3, No. 7, and No. 11.

The pore size distribution was also evaluated along with the porosity. The pore size distribution was evaluated by categorizing the pore sizes of individual pores identified by the above-described image analysis into a plurality of intervals (of 0.1 μm except for the uppermost and lowermost intervals) determined in advance, and calculating the ratio (area ratio) of the total area of pores categorized into each interval to the total area of all pores. FIG. 5 shows the pore size distributions of the gas sensors 100 of No. 3, No. 7, and No. 11 in each of which the surface protective layer 50 has a thickness of 35 μm. The smaller boundary value of each interval on the horizontal axis is included in the interval, and the larger boundary value thereof is not included in the interval.

FIG. 5 indicates that the surface protective layer 50 having a larger porosity has a larger area ratio of coarse pores each having a pore size of 1 μm or larger. In particular, for the gas sensors 100 of No. 7 and 11, the area ratio of the coarse pore is approximately 50% or more.

The evaluation of the sensitivity characteristic to the THC was performed by installing each gas sensor 100 (No. 1 to No. 12) at an exhaust pipe of a diesel engine and measuring the sensor output in cases where the diesel engine was operated under different conditions to generate various exhaust gasses having different THC concentrations. The concentration of the THC was checked by an FID. The element control temperature was 500° C.

Figure 6A:
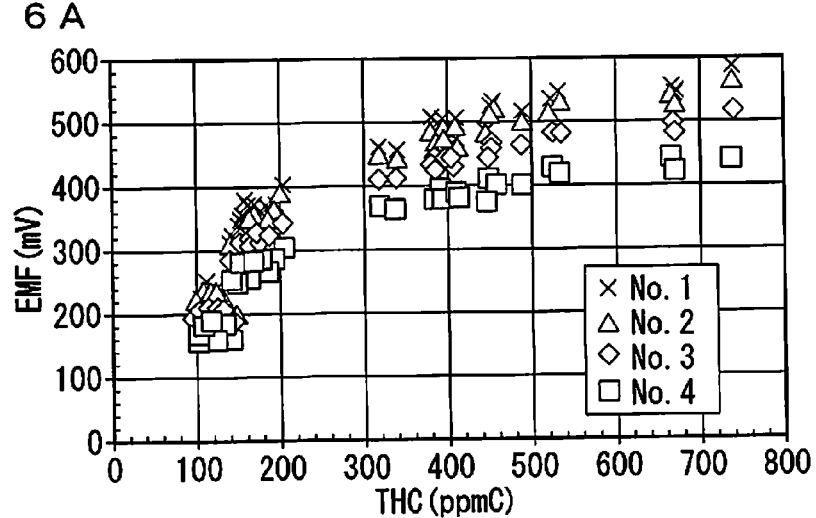
FIGS. 6A, 6B, and 6C show the sensitivity characteristics of the gas sensors 100 of No. 1 to No. 12.
Figure 6B:
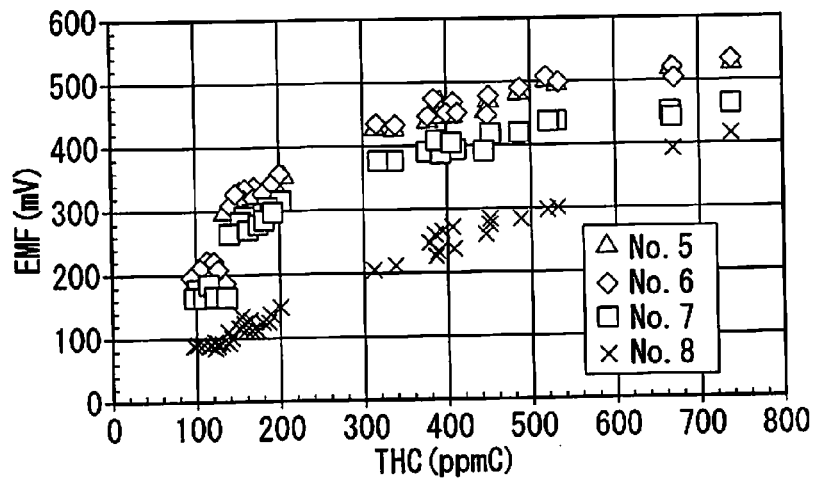
Figure 6C:
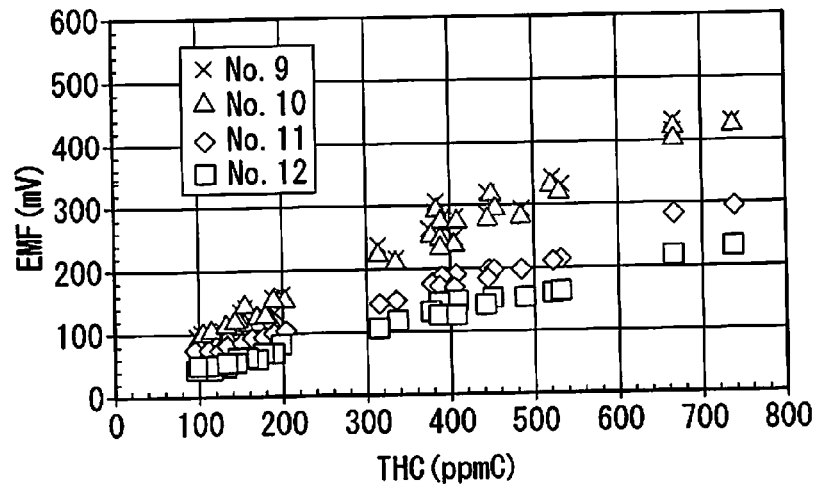

FIGS. 6A, 6B, and 6C show the sensitivity characteristics of the gas sensors 100 of No. 1 to No. 12. FIG. 6A shows the sensitivity characteristics of the gas sensors 100 of No. 1 to No. 4 in each of which the surface protective layer 50 has a porosity of 40%, FIG. 6B shows the sensitivity characteristics of the gas sensors 100 of No. 5 to No. 8 in each of which the surface protective layer 50 has a porosity of 28%, and FIG. 6C shows the sensitivity characteristics of the gas sensors 100 of No. 9 to No. 12 in each of which the surface protective layer 50 has a porosity of 12%. FIGS. 6A, 6B, and 6C indicate that the sensitivity characteristic tends to degrade as the surface protective layer 50 has a smaller porosity or a larger thickness. However, it is also indicated that a sufficient sensor output was obtained irrespective of the thickness in the cases with the porosity of 40% shown in FIG. 6A. It is supposed that this is because, in the gas sensor 100 in which the surface protective layer 50 has a small porosity and a large thickness, any kind of gas having a large C number does not sufficiently pass through the surface protective layer 50 nor reach the sensing electrode 10, and thus the sensor output is not sufficiently obtained.

Table 1 also lists results of the sensitivity characteristic evaluation performed based on FIGS. 6A, 6B, and 6C. The sensitivity characteristic evaluation was performed by assuming measurement of the concentration of the THC halfway through an exhaust path of a diesel engine and a downstream of an oxidative catalyst (DOC), which is expected as one of main usages of the gas sensor 100.

Specifically, since the THC concentration of an exhaust gas having passed through the oxidative catalyst is typically 200 ppmC approximately, it was determined that the sensor is capable of accurately measuring the THC concentration if the sensor output is 300 mV or more for THC=200 ppmC. In Table 1, a circle (○) is given in a "sensitivity characteristics evaluation" column for the gas sensor 100 corresponding to a result of the determination. FIGS. 6A, 6B, and 6C indicate that the gas sensors 100 of No. 1 to No. 7 satisfy this determination criterion.

If the sensor output is 150 mV or more and less than 300 mV for THC=200 ppmC, a measurement accuracy is somewhat inferior, but it was determined that the measurement can be performed at the accuracy that allows at least the use of the sensor in a degradation diagnosis of the DOC. In Table 1, a triangle (Δ) is given in a "sensitivity characteristics evaluation" column for the gas sensor 100 corresponding to a result of the determination. FIGS. 6A, 6B, and 6C indicate that the gas sensors 100 of No. 8 to No. 10 satisfy this determination criterion.

If the sensor output is less than 150 mV for THC=200 ppmC, it was determined that no sufficient sensor output is obtained. In Table 1, a cross (x) is given in a "sensitivity characteristics evaluation" column for the gas sensor 100 corresponding to a result of the determination. FIGS. 6A, 6B, and 6C indicate that the gas sensors of No. 11 and No. 12 satisfy this determination criterion.

The phosphorus poisoning test was performed by installing each gas sensor 100 (No. 1 to No. 12) at an exhaust pipe of a gasoline engine (displacement: 1.8 L) and driving, for 70 hours, the engine using fuel obtained by mixing 0.25 mL of an engine oil additive (lubricant oil additive) as a poisoning substance into 1 L of gasoline.

Then, the surface protective layer 50 before and after the engine drive under the above-described condition was observed by the SEM to determine whether or not the surface protective layer 50 after the drive is clogged due to the poisoning substance. In Table 1, a cross (×) is given in a "poisoning test result" column for the gas sensor 100 at which the clogging occurred, and a circle (○) is given in a "poisoning test result" column for the gas sensor 100 at which no clogging occurred.

Figure 7A:
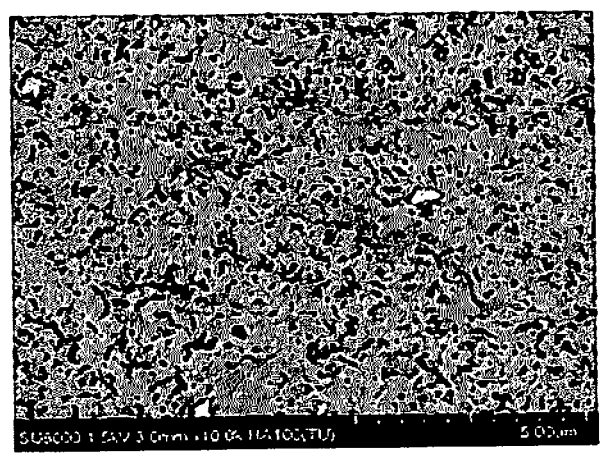
FIGS. 7A and 7B compare SEM images of a surface protective layer of the gas sensor 100 of No. 1 before and after engine drive.
Figure 7B:

Specifically, the clogging occurred in the gas sensors 100 of No. 1, No. 5, and No. 9 to No. 12 in each of which the surface protective layer 50 has a thickness of 5 μm or a porosity of 12%. FIGS. 7A and 7B compare SEM images of the surface protective layer of the gas sensor 100 of No. 1 before and after the engine drive, which exemplarily illustrate the clogging. In FIG. 7A, which illustrates the SEM image before the drive, a large number of fine pores, which appear in black, are distributed. In FIG. 7B, which illustrates the SEM image after the drive, none of such pores are found, but poisoning substances in gray and white are uniformly present.

In addition, the sensitivity characteristics of the gas sensors of No. 1 to No. 3 to $C_2H_4$ and n-C8 ($C_8H_{18}$) before and after the drive were evaluated. Conditions of the element control temperature and the gas atmosphere when the sensitivity characteristics were acquired are same as those of the experimental example.

Figure 8A:
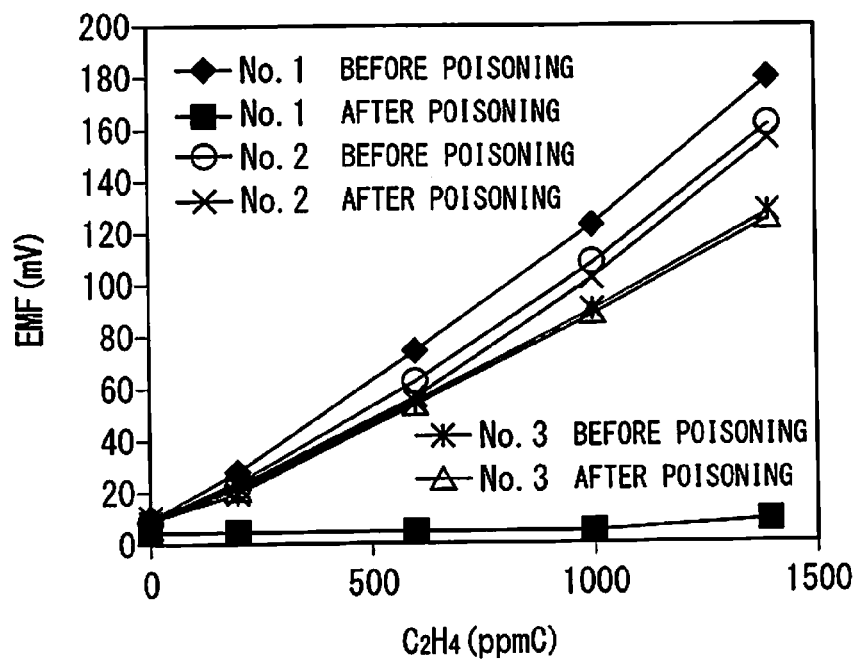
FIGS. 8A and 8B show the sensitivity characteristics of the gas sensors of No. 1 to No. 3 for $C_2H_4$ and n-C8.
Figure 8B:
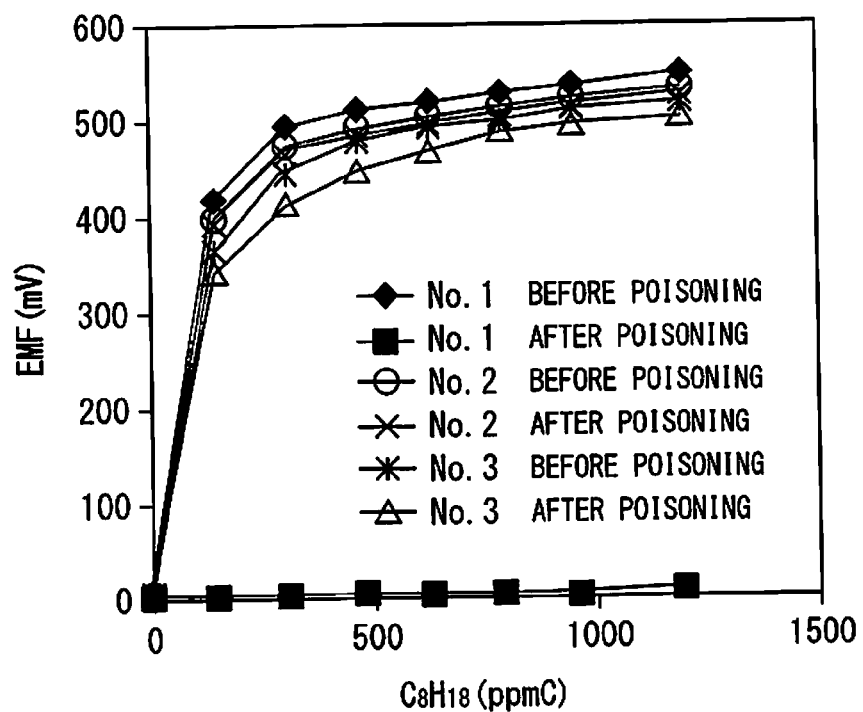

FIGS. 8A and 8B show obtained sensitivity characteristics. FIG. 8A shows a result for $C_2H_4$, and FIG. 8B shows a result for $C_8H_{18}$. In FIGS. 8A and 8B, the label "before poisoning" indicates a sensitivity characteristic acquired before the poisoning test was performed, and the label "after poisoning" indicates a sensitivity characteristic acquired after the poisoning test was performed.

As understood from FIGS. 8A and 8B, after the poisoning test, the gas sensors 100 of No. 2 and No. 3 each substantially maintained a favorable sensitivity characteristic to any kind of gas before the poisoning test. The gas sensor 100 of No. 1 had a favorable sensitivity characteristic before the poisoning test, but after the poisoning test, almost no sensor output was obtained. This result indicates that, once poisoning proceeds in the gas sensor 100 in which the surface protective layer 50 has a small thickness with continuous use, clogging occurs at the surface protective layer 50, preventing measurement, even though it initially has a favorable sensitivity characteristic.

Example 2

In this example, in order to verify influence of a difference in the pore size distribution of the surface protective layer 50 on the performance of the gas sensor 100, a plurality of the gas sensors 100 having the same porosity but different pore size distributions were prepared to perform the evaluation of the pore size distribution, the evaluation of the sensitivity characteristic to THC, and the phosphorus poisoning test, similarly to the example 1.

Specifically, 12 kinds of the gas sensor 100 (No. 13 to No. 16 of type A, No. 5 to No. 8 of type B, and No. 17 to No. 20 of type C) in each of which the surface protective layer 50 has a porosity of 28%, the pore size distribution was varied in three levels (types A to C), and the thickness was varied in four levels: 5 μm, 10 μm, 35 μm, and 50 μm. The gas sensors 100 belonging to type B are same as the gas sensors 100 of No. 5 to No. 8 in the example 1. The Au abundance ratio was 0.50 for any gas sensor 100.

Table 2 lists a combination of the pore size distribution type and the thickness of the surface protective layer 50 of each gas sensor 100.

TABLE 2

| SENSOR NO. | PORE SIZE DISTRIBUTION | PROTECTIVE LAYER THICKNESS (μm) | SENSITIVITY CHARACTERISTIC EVALUATION | POISONING TEST RESULT |
|---|---|---|---|---|
| 13 | TYPE A | 5 | ○ | × |
| 14 | TYPE A | 10 | ○ | ○ |
| 15 | TYPE A | 35 | Δ | ○ |
| 16 | TYPE A | 50 | × | ○ |
| 5 | TYPE B | 5 | ○ | × |
| 6 | TYPE B | 10 | ○ | ○ |
| 7 | TYPE B | 35 | ○ | ○ |
| 8 | TYPE B | 50 | Δ | ○ |
| 17 | TYPE C | 5 | ○ | × |
| 18 | TYPE C | 10 | ○ | ○ |
| 19 | TYPE C | 35 | ○ | ○ |
| 20 | TYPE C | 50 | ○ | ○ |

At the preparation of each gas sensor 100, the pore size distributions of types A to C and the porosity of 28% were achieved by adjusting a preparation condition of a protective-layer paste and the firing temperature at the manufacture of the sensor element 101. The following lists specific conditions.

Type A: the protective-layer paste was prepared by using an alumina raw material having a relative surface area of 60 $m^2/g$ as the raw material of the surface protective layer 50, and the sensor element 101 was manufactured at a firing temperature of 1300° C.;

Type B: the protective-layer paste was prepared by using an alumina raw material having a relative surface area of 8.4 $m^2/g$ as the raw material of the surface protective layer 50, and the sensor element 101 was manufactured at a firing temperature of 1370° C.; and Type C: the protective-layer paste was prepared by using an alumina raw material having a relative surface area of 60 $m^2/g$ as the raw material of the surface protective layer 50 and by mixing acrylic resin as a pore forming material, and the sensor element 101 was manufactured at a firing temperature of 1370° C.

FIG. 9 shows pore size distributions obtained for the gas sensors 100 of No. 15, No. 7, and No. 19 in each of which the surface protective layer 50 has a thickness of 35 μm, similarly to the example 1. Although not shown, it has been found that, as long as formed by the same method, the surface protective layer 50 has the same pore size distribution with different thicknesses.

FIG. 9 indicates that different pore size distributions were actually achieved between types A to C with the same porosity. More specifically, the area ratio of the coarse pore was smallest for type A and largest for type C, and was about 50% or more for the gas sensors 100 of type B and type C.

FIGS. 10A, 10B, and 10C show the sensitivity characteristics of all gas sensors 100 of types A to C. FIG. 10A shows the sensitivity characteristics of the gas sensors 100 of No. 13 to No. 16 in each of which the surface protective layer 50 has a pore size distribution of type A, FIG. 10B shows the sensitivity characteristics of the gas sensors 100 of No. 5 to No. 8 in each of which the surface protective layer 50 has a pore size distribution of type B, and FIG. 10C shows the sensitivity characteristics of the gas sensors 100 of No. 17 to No. 20 in each of which the surface protective layer 50 has a pore size distribution of type C. Table 2 also lists results of the sensitivity characteristic evaluation performed based on FIGS. 10A, 10B, and 10C. The determination criterion was same as that in the example 1.

FIGS. 10A, 10B, and 10C indicate that relatively large sensor outputs were obtained for the gas sensors 100 of type B and type C each having the area ratio of the coarse pore of 50% approximately or more. In particular, it is indicated that substantially same sensitivity characteristics were obtained for the gas sensors 100 of No. 5 to No. 7 and No. 17 to No. 19. In addition, it was determined that only these gas sensors 100 are capable of accurately measuring the concentration of the THC in the sensitivity characteristic evaluation (as indicated by circles in Table 2). This indicates that, in these gas sensors 100, each kind of gas contained in the THC, such as a kind of gas having a large C number, reliably reaches the sensing electrode 10, so that the concentration of the THC can be accurately measured.

In the sensitivity characteristic evaluation, the gas sensors 100 of No. 13 to No. 15, No. 8, and No. 20 were determined to be capable of performing measurement at least at an accuracy allowing the use of the sensor in a degradation diagnosis of the DOC (as indicated by triangles in Table 2). It is also determined that no sufficient sensor output was obtained for only the gas sensor 100 of No. 16 (as indicated by cross in Table 2).

Table 2 also lists the occurrence of clogging at the surface protective layer 50 after the poisoning test, based on a criterion same as that in the example 1.

Specifically, the clogging occurred to the gas sensors 100 of No. 13, No. 5, and No. 17 of types A to C in each of which the surface protective layer 50 has a thickness of 5 μm.

Summary of Example 1 and Example 2

In the examples 1 and 2 described above, the gas sensors 100 of No. 2 to No. 4, No. 6, No. 7, No. 18, and No. 19 are each determined to have a sensitivity characteristic allowing accurate THC concentration measurement and not to suffer the occurrence of clogging at the surface protective layer 50 due to a poisoning substance (as indicated by circles in "sensitivity characteristics evaluation" columns and circles in "poisoning test result" columns in Tables 1 and 2).

The gas sensors 100 of No. 8, No. 14, No. 15, and No. 20 are each determined to have an insufficient accuracy of THC concentration measurement but a sensitivity characteristic allowing a degradation diagnosis of the DOC and not to suffer the occurrence of clogging at the surface protective layer 50 due to a poisoning substance (as indicated by triangles in "sensitivity characteristics evaluation" columns and circles in "poisoning test result" columns in Tables 1 and 2).

These results indicate that the gas sensor 100, the surface protective layer 50 of which satisfies at least the second condition, can sense, at least at a level allowing its practical use, THC including a hydrocarbon having a large C number, and does not suffer the occurrence of clogging of the surface protective layer 50 due to a poisoning substance when continuously used. The results also indicate that the gas sensor 100, the surface protective layer 50 of which satisfies the first condition, can sense almost all hydrocarbons included in the THC and measure the THC at an excellent accuracy.

While the invention has been shown and described in detail, the foregoing description is in all aspects illustrative and not restrictive. It is therefore understood that numerous modifications and variations can be devised without departing from the scope of the invention.

What is claimed is:

1. A mixed-potential type gas sensor for sensing a hydrocarbon gas in a measurement gas, said sensor comprising a sensor element composed of an oxygen-ion conductive solid electrolyte, said sensor element including:
a sensing electrode formed of a cermet of a noble metal and an oxygen-ion conductive solid electrolyte, said sensing electrode being provided on a surface of said sensor element;
a reference electrode formed of a cermet of Pt and an oxygen-ion conductive solid electrolyte; and
a surface protective layer being a porous layer that covers at least said sensing electrode, wherein
said noble metal is Pt and Au,
an Au abundance ratio is 0.3 or more, said Au abundance ratio being an area ratio of a portion covered with said Au to a portion at which said Pt is exposed in a surface of noble metal particles forming said sensing electrode,
said surface protective layer has:
a porosity of 28% or more and 40% or less, a thickness of 10 μm or larger and 50 μm or smaller, and an area ratio of a coarse pore of 50% or more, the area ratio of the coarse pore being a ratio of an area of coarse pores each having a pore size of 1 μm or larger to the total area of all pores, or
a porosity of 28% or more and 40% or less and a thickness of 10 μm or larger and 35 μm or smaller, and
said sensor element is configured and arranged to determine a concentration of said hydrocarbon gas on the basis of a potential difference between said sensing electrode and said reference electrode.

2. The gas sensor according to claim 1, wherein said surface protective layer has a porosity of 28% or more and 40% or less, a thickness of 10 μm or larger and 35 μm or smaller, and the area ratio of the coarse pore of 50% or more.

3. The gas sensor according to claim 1, wherein the Au abundance ratio is 0.3 or more in an entirety of the sensing electrode.

* * * * *